(12) United States Patent
Scurtescu et al.

(10) Patent No.: US 11,890,355 B2
(45) Date of Patent: Feb. 6, 2024

(54) VISCOSITY AND STABILITY MODIFIED ULTRASOUND GEL

(71) Applicant: SmileSonica Inc., Edmonton (CA)

(72) Inventors: Cristian Scurtescu, Edmonton (CA); Gleam Gill, Edmonton (CA)

(73) Assignee: Smilesonica Inc., Edmonton (CA)

( * ) Notice: Subject to any disclaimer, the term of this patent is extended or adjusted under 35 U.S.C. 154(b) by 0 days.

(21) Appl. No.: 16/797,813

(22) Filed: Feb. 21, 2020

(65) Prior Publication Data

US 2020/0188538 A1 Jun. 18, 2020

Related U.S. Application Data

(62) Division of application No. 16/068,946, filed as application No. PCT/CA2016/051452 on Dec. 9, 2016, now abandoned.

(60) Provisional application No. 62/276,927, filed on Jan. 10, 2016.

(51) Int. Cl.
| | |
|---|---|
| *A61K 31/047* | (2006.01) |
| *A61K 49/22* | (2006.01) |
| *A61N 7/00* | (2006.01) |
| *A61K 47/38* | (2006.01) |
| *A61K 9/06* | (2006.01) |
| *A61B 8/00* | (2006.01) |
| *A61K 47/10* | (2017.01) |
| *A61K 47/26* | (2006.01) |
| *A61K 47/32* | (2006.01) |
| *A61B 8/12* | (2006.01) |
| *A61B 17/225* | (2006.01) |

(52) U.S. Cl.
CPC .......... *A61K 49/226* (2013.01); *A61B 8/4281* (2013.01); *A61K 9/06* (2013.01); *A61K 47/10* (2013.01); *A61K 47/26* (2013.01); *A61K 47/32* (2013.01); *A61K 47/38* (2013.01); *A61N 7/00* (2013.01); *A61B 8/12* (2013.01); *A61B 2017/2253* (2013.01)

(58) Field of Classification Search
None
See application file for complete search history.

(56) References Cited

U.S. PATENT DOCUMENTS

| | | | | |
|---|---|---|---|---|
| 8,273,024 B2* | 9/2012 | Chew | .................. | A61B 8/4281 600/437 |
| 8,828,434 B2* | 9/2014 | Su | .......................... | B82Y 30/00 424/484 |
| 2012/0237612 A1* | 9/2012 | Lampe | .................. | A01N 47/44 424/618 |
| 2013/0116331 A1* | 5/2013 | Heinar | .................. | A61K 31/14 514/643 |
| 2016/0002457 A1 | 1/2016 | Hamad et al. | | |

FOREIGN PATENT DOCUMENTS

| | | |
|---|---|---|
| CA | 2970146 A1 | 6/2016 |
| CN | 101695576 A | 10/2009 |
| CN | 102580122 A | 7/2012 |
| EP | 0393299 A1 | 10/1990 |
| JP | 2008508338 | 3/2008 |
| WO | 2006013081 | 2/2006 |
| WO | 2014085730 A1 | 6/2014 |
| WO | 2014094127 A1 | 6/2014 |
| WO | WO-2014094127 A1 * | 6/2014 ........... A61B 8/4281 |

OTHER PUBLICATIONS

Yang et al (Mechanical and Viscoelastic Properties of Cellulose Nanocrystals Reinforced Poly(ethylene glycol) Nanocomposite Hydrogels. ACS Appl. Mater. Interfaces 2013, 5, 8, 3199-3207) (Year: 2013).*
Shen et al (Hydrogels based on cellulose and chitin: fabrication, properties, and applications. Green Chem., 2016, 18, 53 (published online Nov. 16, 2015)). (Year: 2016).*
Shafiei-Sabet, S. et al. "Rheology of Nanocrystalline Cellulose Aqueous Suspensions", Langmuir, 28, 17124-17133.
New Zealand Intellectual Property Office Examination Report, dated Dec. 7, 2020, Application No. 744196.
The Effective use of Oral Moisturizers, Akemi Yamaguchi, 2010.
JP Office Action dated Jun. 23, 2020.
Hu et al. "Synergistic stabilization of emulsion and emulsion gels with water-soluble polymers and cellulose hanocrystals" Sustainable Chemistry & Engineering, 2015, vol. 3, pp. 1023-1031.
Yang et al. "Injectable polysaccharide hydrogels reinforced with cellulose nanocrystals: Morphology, Rheology, degradation, and cytotoxicity", BioMacromolecules, 2013, vol. 4447-4455.
Yang, C., Xu, L., Zhou, Y., Zhang, X., Huang, X., Wang, M., . . . Li, J. (2010). A green fabrication approach of gelatin/CM-chitosan hybrid hydrogel for wound healing. Carbohydrate Polymers, 82(4), 1297-1305. doi: 10.1016/j.carbpol.2010.07.013.
Zhang, X., Xu, L., Huang, X., Wei, S., & Zhai, M. (2012). Structural study and preliminary biological evaluation on the collagen hydrogel crosslinked by γ-irradiation. Journal of Biomedical Materials Research Part A, 100A(11), 2960-2969. doi:10.1002/jbm.a.34243.

(Continued)

*Primary Examiner* — Jake M Vu
(74) *Attorney, Agent, or Firm* — Russell Manning; FisherBroyles, LLP (57) ABSTRACT

An ultrasound gel is provided for use with internal ultrasound imaging and/or therapy. The gel can have acoustic properties that can closely match a soft tissue to be imaged/treated and can be of a high viscosity that is maintained at body temperature. In some embodiments, the gel can act as a lubricant and, although water based, can be hydrophobic and not dissolve in bodily fluids. In some embodiments, the gel can be sterile, safe for ingestion, safe for application over mucous membranes, and include a preservative. In order to achieve sterility while maintaining a desired viscosity range, the gel can include a viscosity stabilising agent such as a viscosity protection agent for protection from radiation induced breakdown. In some embodiments, methods of altering or maintaining the viscosity of a gel is provided.

11 Claims, 1 Drawing Sheet

(56) References Cited

OTHER PUBLICATIONS

Wisotzki, E. I., Hennes, M., Schuldt, C., Engert, F., Knolle, W., Decker, U., . . . Mayr, S. G. (2014). Tailoring the material properties of gelatin hydrogels by high energy electron irradiation. J. Mater. Chem. B, 2(27), 4297-4309. doi:10.1039/c4tb00429a.
Sabet S.S. Ph.D. Thesis. University of British Columbia Library; Vancouver, BC, Canada: 2013. Shear Rheology of Cellulose Nanocrystal (CNC) Aqueous Suspensions.
Shafiei-Sabet, S., Hamad, W. Y., & Hatzikiriakos, S. G. (2014). Ionic strength effects on the microstructure and shear theology of cellulose nanocrystal suspensions. Cellulose, 21(5), 3347-3359. doi:10.1007/s10570-014-0407-z.
Heath, L., & Thielemans, W. (2010). Cellulose nanowhisker aerogels. Green Chemistry, 12(8), 1448. doi: 10.1039/c0gc00035c.

\* cited by examiner

VISCOSITY AND STABILITY MODIFIED ULTRASOUND GEL

CROSS REFERENCE TO RELATED APPLICATIONS

This application a divisional application of U.S. patent application Ser. No. 16/068,946 entitled "Viscosity and Stability Modified Ultrasound Gel," filed Jul. 10, 2018 which is a National Stage under 37 U.S.C. 371 of International Application No. PCT/CA2016/051452, entitled "Viscosity and Stability Modified Ultrasound Gel," filed Dec. 9, 2016, which claims the benefit of U.S. Provisional Patent Application No. 62/276,927, entitled "Viscosity and Stability Modified Ultrasound Gel," filed Jan. 10, 2016, and hereby incorporated by reference herein in their entireties.

TECHNICAL FIELD

The present application relates to ultrasound gels and, more particularly, ultrasound gels that can be safely used internally and/or orally.

BACKGROUND

By way of background, it is standard practice to use aqueous gels as coupling agents for ultrasound producing/sensing devices in ultrasound imaging and therapy. A key element of an ultrasound gel is to have acoustic impedance similar to that of soft tissue. Some ultrasound therapies and imaging are done by inserting an ultrasound probe into a body cavity (intracavitary ultrasound procedures) or otherwise internally into a patient. For example, ultrasonic dental therapy or imaging devices require the patient to apply the gel intra-orally, however there is presently no known ultrasonic gel product specifically approved and labelled for intra-oral applications. While there are existing non-ultrasonic intra-oral gels, the gels are still labelled as "not to be ingested". The use of a gel with ultrasonic dental therapy or oral/intracavitary imaging devices requires the patient to apply the gel intra-orally, which can lead to ingestion of small quantities of gel.

Some gels face difficulty in maintaining the gel viscosity high after gamma radiation sterilization. For example, a gel may have a target viscosity in the order of 80,000 cPs (centipoises) –100,000 cPs after sterilization with gamma radiation, however where the initial gel is very viscous (>100,000 cPs) before gamma radiation sterilization, after the gel is exposed to gamma radiation (for example, a 25-40 kGy standard dose for sterilization used in the industry) it becomes a near liquid of very low viscosity (for example, less than 10,000 cPs).

Accordingly, a solution is desired to obtain a gel compatible with gamma irradiation (for sterilization) and has a high post-irradiation viscosity (80,000-100,000 cPs) usable for intracavitary ultrasound where high viscosity and sterility is required. As such, there remains a need to provide products and methods, such as internally and orally compatible ultrasound gels, that can overcome the shortcomings of the prior art.

SUMMARY

The present disclosure relates to an ultrasound gel for use with internal and oral ultrasound imaging and/or therapy. The gel can have ultrasound acoustic properties that can closely match a soft tissue to be imaged/treated and can be of a high viscosity that is maintained at body temperature or when exposed to bodily fluids (for instance, saliva). In some embodiments, the gel can act as a lubricant. Although water-based, the gel can be hydrophobic and not readily dissolvable in bodily fluids. In some embodiments, the gel can be sterile, safe for ingestion, and include a preservative. The gel can be used for oral or non-oral applications and when used orally, can comprise a dental agent for inhibiting growth of dental microorganisms. In order to achieve sterility while maintaining a desired viscosity range, the gel can include a viscosity stabilising agent such as a viscosity protection agent for protection from radiation induced breakdown. In some embodiments, methods of altering or maintaining the viscosity of a gel is provided.

In some embodiments, the gels can provide an ultrasound couplant and device lubricant suitable for medical use of ultrasound acoustic energy for intra-oral and dental therapy, intracavitary ultrasound imaging or other measurements, while contacting the intra-oral, dental tissue or food pipe tissue, mucous membranes, fluids and neighbouring/adjacent organs. The gel can have acoustic properties similar to soft tissue or gums, or other internal bio-structures.

The term "CNC", as used herein, can refer to Cellulose Nanocrystals, Crystalline Nanocellulose, and is also known as Nanocrystalline Cellulose (NCC). CNC can be a polymer and can comprise nanoparticles in some embodiments.

CNC can have cross-linkage properties and can disperse in water. Polymeric systems based on cellulose with responsive behaviors can show unique properties such as biocompatibility, biodegradability, and biological functions.

Use of CNC according to the present disclosure, can provide for at least two new and unexpected behaviours:
  a) addition of small amounts of CNC can maintain high viscosity of a carbomer based ultrasound gel after undergoing gamma radiation sterilization. Adding CNC can reduce or prevent a gel viscosity drop observed during shelf life testing post irradiation. In addition, to achieving a high viscosity pre and post radiation, the use of small concentrations of CNC can allow the use of less highly cross-linked Carbopol™. For example, there are various grades of Carbopol™ available, some with higher cross-linking than others.
  b) gels made of only CNC (no carbomer) and water increased gel viscosity after exposure to gamma radiation.

The state of the art does not teach:
  a) the use of CNC as an additional gelling agent in carbomer based ultrasound gels. The use of CNC as an additional component (a few % by mass being added) in ultrasound gel based on a carbomer gelling agent (such as Carbopol™), can increase the viscosity of the resulting gel, while maintaining appropriate acoustic properties of the gel;
  b) the use of CNC as a protection agent in carbomer based ultrasound gels against the loss in viscosity caused by gamma radiation sterilization. Where CNC is added to a ultrasound gel based on a carbomer gelling agent (such as Carbopol™), and the gel is sterilized using gamma radiation, the resulting post radiated gel can remain much more viscous (for example, twice as viscous) as compared with a post radiated gel that did not have any CNC added; and
  c) the thickening behavior of CNC gels (just CNC, without carbomer) when irradiated during gamma radiation sterilization. CNC gels (without carbomer) can increase their viscosity when irradiated with gamma rays, and this can provide a method to obtain high viscosity ultrasound gels post radiation, and control the viscosity post radiation by controlling the radiation dose and the initial CNC concentration in pre-radiation gel.

Regarding the term "Carbopol™", as used herein, can refer to high molecular weight, crosslinked polyacrylic acid polymers. Carbopols™ can differ by crosslink density and can be grouped as homopolymers or copolymers. Carbopol™ homopolymers can be polymers of acrylic acid crosslinked with allyl sucrose or allyl pentaerythritol. Carbopol™ 974P NF is a homopolymer (acrylic acid crosslinked with allyl pentaerythritol). Carbopol™ copolymers can be polymers of acrylic acid and C10-C30 alkyl acrylate crosslinked with allyl pentaerythritol.

The term "carbomer", as used herein, is a generic (i.e. nonproprietary) name adopted by USP-NF, United States Adopted Names Council (USAN) and CTFA for various Carbopol™ polymers. As such Carbopol™ 974P NF can be referred to as a carbomer homopolymer Type B. Carbomers 71G and 971P NF are categorized as Homopolymer Type A, while 974P NF is Type B based on their viscosity characteristics.

Broadly stated, in some embodiments, an internal ultrasound gel is provided, comprising: water; a thickening agent for thickening the water into a gel; a neutralizer for setting the gel viscosity and adjusting a pH level of the gel; a viscosity agent for reducing changes of gel viscosity due to radiation exposure; and a preservative for preserving the gel; wherein the gel has an acoustic impedance similar to soft tissue and can be safely used internally or orally.

In some embodiments, the viscosity agent comprises nanoparticles, CNC, and/or glycerin. In some embodiments, the thickening agent comprises a carbomer, a Carbopol™, and/or carbomer homopolymer Type B (Carbopol™ 974P NF). In some embodiments, the neutralizer comprises a base selected from the group consisting of potassium hydroxide, sodium hydroxide, and triethanolamine and the pH level of the gel is between 5.8 and 6.4. In some embodiments, the preservative comprises a food grade preservative and/or potassium sorbate. In some embodiments, the gel further comprises a dental agent for inhibiting growth of dental microorganisms, such as, but not limited to a sugar alcohol, such as, but not limited to, xylitol. In some embodiments, the gel further comprises a colourant for colouring the gel.

Broadly stated, in some embodiments, a method of imaging a tissue with ultrasound is provided, the method comprising: providing an ultrasound imaging apparatus, the apparatus comprising a transducer for emitting ultrasound; applying an ultrasound gel, as described herein, between the transducer and the tissue to be imaged; positioning the transducer proximate the tissue to be imaged; and emitting ultrasound through the gel to image the tissue.

Broadly stated, in some embodiments, a method of treating a tissue with ultrasound is provided, the method comprising: providing an ultrasound treatment apparatus, the apparatus comprising a transducer for emitting ultrasound; applying an ultrasound gel, as described herein, between the transducer and the tissue to be treated; positioning the transducer proximate the tissue to be treated; and emitting ultrasound through the gel to treat the tissue.

Broadly stated, in some embodiments, a kit for applying ultrasound to a tissue is provided, the kit comprising, an ultrasound gel, as described herein, and instructions for use of the gel.

Broadly stated, in some embodiments, a method of protecting a viscosity of a polymer based ultrasound gel is provided, the method comprising: providing an ultrasound gel comprising water; a thickening agent for thickening the water into a gel; a neutralizer for setting the gel viscosity and adjusting a pH level of the gel; and a preservative for preserving the gel; wherein the gel has an acoustic impedance similar to soft tissue and can be safely used internally or orally; adding a viscosity agent to the ultrasound gel for reducing changes of ultrasound gel viscosity due to radiation exposure; and exposing the ultrasound gel to radiation; wherein a decrease in ultrasound gel viscosity, due to exposure to radiation, is reduced by the viscosity agent.

In some embodiments, the viscosity agent comprises nanoparticles, CNC, and/or glycerin.

Broadly stated, in some embodiments, a method of altering the viscosity of a gel is provided, the method comprising: providing a gel precursor comprising water; creating a mixture by adding a viscosity agent to the gel precursor, the viscosity agent for altering viscosity of the gel precursor due to radiation exposure; and exposing the mixture to radiation; wherein an alteration in mixture viscosity changes, due to exposure to radiation, is caused by the viscosity agent.

In some embodiments, the viscosity agent comprises nanoparticles, CNC, and/or glycerin.

Broadly stated, in some embodiments, an internal ultrasound gel is provided, said ultrasound gel as produced by any of methods disclosed herein.

Broadly stated, in some embodiments, a use of CNC as a viscosity agent is provided to cause a decrease a change to ultrasound gel viscosity due to exposure to radiation.

Broadly stated, in some embodiments, a use of CNC as a viscosity agent is provided to cause an alteration in hydrogel viscosity changes due to exposure to radiation.

DETAILED DESCRIPTION OF EMBODIMENTS

An ultrasound gel is provided for use with internal and oral ultrasound imaging and/or therapy. The gel can have ultrasound acoustic properties that can closely match a soft tissue to be imaged/treated and can be of a high viscosity that is maintained at body temperature or when exposed to bodily fluids (for instance, saliva). In some embodiments, the gel can act as a lubricant. Although water-based, the gel can be hydrophobic and not readily dissolvable in bodily fluids. In some embodiments, the gel can be sterile, safe for ingestion, and include a preservative. The gel can be used for oral or non-oral applications and when used orally, can comprise a dental agent for inhibiting growth of dental microorganisms. In order to achieve sterility while maintaining a desired viscosity range, the gel can include a viscosity stabilising agent such as a viscosity protection agent for protection from radiation induced breakdown. In some embodiments, methods of altering or maintaining the viscosity of a gel is provided.

Figure 1:
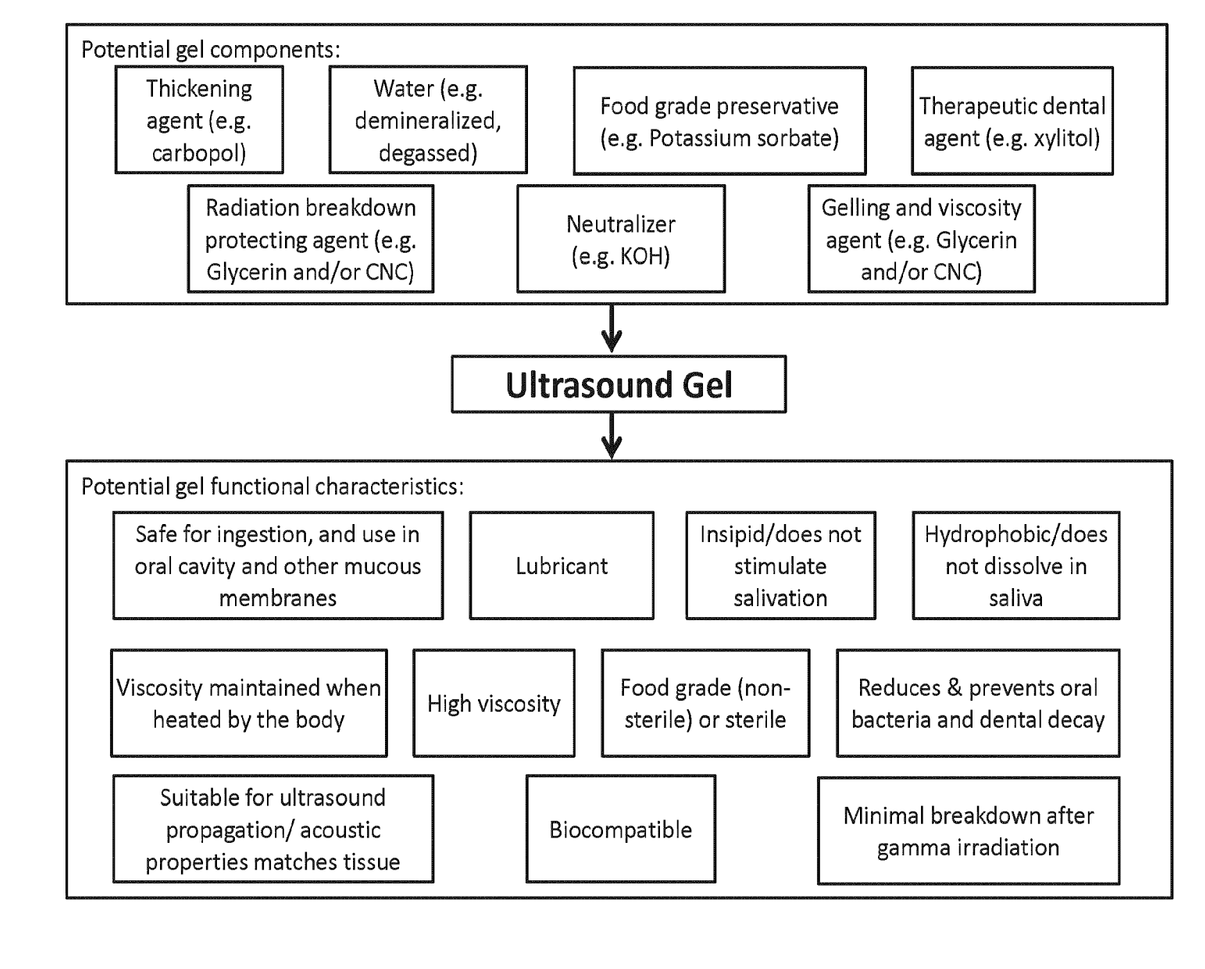
FIG. 1 is a schematic block diagram depicting an embodiment of an ultrasound gel.

Referring now to FIG. 1, a schematic block diagram is shown depicting possible components and potential functional characteristics of an embodiment of an ultrasound gel. In some embodiments, the ultrasound gel can comprise a thickening agent, water, a neutralizer, a preservative, a viscosity affecting agent/a radiation breakdown protective agent, and a dental agent. In some embodiments, the ultrasound gel can be biocompatible, safe for ingestion and application over mucous membranes, insipid, hydrophobic, of high viscosity that can be maintained when heated, food grade and/or sterile, reduce and prevent oral bacteria and dental decay, suitable for ultrasound propagation/acoustic properties match soft tissue, have reduced viscosity breakdown following exposure to gamma irradiation, and also be a good lubricant.

In some embodiments, the gel can be used as a medical ultrasound coupling media and lubricant. The gel can possess certain properties as outlined herein.

In some embodiments, the gel can be biocompatible, orally compatible, mucous membrane compatible, and ingestible by humans or animals. The components of the gel can be based on the U.S. Food and Drug Administration (FDA) Generally Recognized as Safe (GRAS) list and/or Food Additive Status list for acceptable ingredients and additives. In some specific embodiments, the gel components can be Carbopol™ 974P NF, water, potassium sorbate, potassium hydroxide, glycerine, CNC, and/or xylitol, with an acidity at a non-irritating level (for example, between pH 5.5 and 7.5, and in some embodiments, pH 6.0). As all gel components can be safe for ingestion and mucous membrane application, the gel will be safe if a patient ingests the gel accidentally or intentionally. In some embodiments, the gel can be food grade, following good manufacturing practice (GMP) or natural health products (NHP) standards, or sterile. The gel can be sterilized by heat (for example, by autoclaving) or other sterilization methods as known in the art (for example, by e-beam or gamma irradiation). In sterile embodiments, the gel can also be used on open wounds. In some embodiments, the gel can be safe for long term repeated ingestion. For example, users can ingest small quantities (a few mL) daily without adverse effects as per FDA's GRAS database. The gels can be excretable by natural pathways or processes. In some embodiments, the gels also do not adversely affect tooth health, gum tissue, or corrode teeth.

In some embodiments, the gel formulation may require additional compounds in order to maintain its integrity through sterilization, for example gamma radiation sterilization. These stability compounds can include, for example, glycerine (glycerol) or propylene glycol. Glycerol has very low toxicity when ingested and it is used widely in foods, beverages, and personal care preparations. The oral toxicity of propylene glycol is also very low, and it does not cause sensitization. Glycerol and propylene glycol can also be compatible with (and not damage) ultrasound transducer encapsulation such as commonly used silicone.

Different strategies can be used to achieve a gel of a certain viscosity. Glycerine, for example, can be added to an initial gel formulation in order to protect the gel during gamma radiation sterilization. In addition, a sterilizing radiation dosage can be kept as low as possible (for example, a 25-40 kGy standard dose for sterilization used in the industry). Further, increasing the concentration of the polymer (for example Carbopol™) in the gel so that the resulting radiated gel will be thicker. These modifications, however, do still not result in a solution to the problem of creating a gel has a target viscosity in the order of 80,000 cPs-100,000 cPs after sterilization with gamma radiation.

Further increases in the concentration of Carbopol™ in the gel to increase its viscosity cannot create a safe internal and ingestible ultrasound gel as the higher amount of Carbopol™ will be potentially ingested by a patient during each use, leading to safety concerns.

Adjusted gel viscosities also push the manufacturing of the gel into a less predictable outcome and the manufacturability of such a product is constrained. For example, there is a limit to reducing the radiation dose exposure to the gel while ensuring a minimum exposure of 25 KGy dose. When irradiating the gel, with the minimum exposure set at 25 KGy a feasible dose range is required (while following the VDmax method for sterilization validation). Hence, the gel still will be exposed to a radiation dose much higher than 25 KGy. As such, the industry practice for sterile products is to develop a formulation that remains stable for the maximum gamma radiation dose of 40 kGy or higher, which will ensure that the normal dose of 25-40 kGy used in the industry will always result in post-irradiation products with the desired parameters.

An example is provided using the following terminology and formulations:
a) "Initial Gel" formulation (per 100 g of gel): 1.3 g Carbopol™, 4.29 g of 18% KOH, 0.5 g xylitol, 0.1 g Potassium Sorbate (optional), and the rest demineralized water, all mixed under vacuum; and
b) "Adjusted gel" formulation (per 100 g of gel): 1.8 g Carbopol™, 9.5 g glycerine, 4.29 g KOH, 0.5 g xylitol, 0.1 g Potassium Sorbate (optional), and the rest demineralized water, all mixed under vacuum.

The viscosity of the adjusted gel before irradiation was approximately 94,500 cPs (formulation of 1.3% Carbopol™ with 5% glycerin), however, viscosity can be >100,000 cPs with an increase in Carbopol™ from 1.3 g to 1.8 g. The viscosity of the adjusted gel after irradiation (range 27.6-32.8 kGy) was 85,000 cPs, being on the lower side of a desired range (80,000-100,000). When viscosity was re-measured after a few months, viscosity had decreased significantly. Using frequent viscosity measurements, viscosity continued to decrease and stabilized at around 65,000 cPs after 11 months of storage at room temperature. While this is still considered a thick gel in industry terms, the viscosity is lower than initially desired for medical/dental applications and it has to be thick so that it stays firm on ultrasound devices and limits the amount of gel that is washed away by bodily fluids, such as saliva and then ingested.

While the adjusted gel can be used for dental applications, because it viscosity is lower than desired, its applicability for other ultrasound applications (such as intracavitary ultrasound) is less and less of an option or fit. For example, the adjusted gel viscosity of 65000 cPs after radiation compares to existing sterile and non-sterile ultrasounds gels on the market (30,000-45,000 cPs).

In some embodiments, a small amount of glycerol (from a few percent to a few tens of percent) can be used to enhance gel resistance to breaking down under larger doses of gamma radiation. For oral use of a gel, a low glycerol concentration (for example, 5%-10%) can be used without significantly sweetening the gel, while allowing the gel to withstand larger dose of gamma radiation (for example 40 kGy) and maintaining the high viscosity of the gel post-irradiation.

A low glycerol concentration (5%-10%) can also cause a negligible increase in the acoustic impedance of the gel therefore maintaining an acoustic impedance closely similar to that of soft tissue (approximately 1.5 MRayl), which can be important for ultrasound wave propagation to minimize transducer-gel-tissue interface ultrasound reflections.

In addition, some embodiments of the gels can also be safe for use with ultrasound transducer equipment, such as ultrasound transducers and transducer heads known to those skilled in the art (including materials such as silicone elastomers, epoxy, or plastic, for instance). Accordingly, the gels can be used with ultrasound equipment without causing damage to the equipment. In some embodiments, the gel can be complementary to, and easily incorporated within, intra-oral ultrasonic devices and emerging ultrasonic dental imaging systems.

In some embodiments, the gels can have antimicrobial properties. For example, the gels can resist microbial growth after the gel package/bottle is opened, and after possible contamination by the environment or end user. In some embodiments, a preservative can be used to inhibit molds, yeasts and bacteria in the gel. In some embodiments, the gels can have a long shelf life at room temperature. When under proper conditions, some embodiments of the gel can be shelf-stable and will not physically degrade/decompose at room temperature for a period of approximately at least two years and can also be resistant to microbial spoilage for approximately at least two years.

In some embodiments, the gel can both comprise a preservative and also be sterilized as discussed herein. In these embodiments, the combination of preservative and sterilization can provide for additional safety for usage in internal or oral applications.

In some embodiments, the gels can have a high viscosity as would be understood by one skilled in the art. Viscosity can be difficult to quantify and measure and the measurement can be dependent on the measuring apparatus used and the conditions under what the viscosity is measured. Having said that, one skilled in the art would have a working knowledge of the relative viscosity of a gel with high viscosity. The viscosity and pH can be of an appropriate level to be comfortable and non-irritating to a user. In addition, in some embodiments, the viscosity of the gel is not significantly affected/reduced when the gel heats up in contact with tissue/gums/saliva. The gel can also be able to withstand environments it is exposed to during ultrasound imaging/treatment without a change in viscosity characteristics. Gel viscosity and acoustic impedance can continue to be within acceptable imaging/treatment ranges even after use as intended.

The gel can act as an ultrasound couplant and the high viscosity can provide good acoustic coupling to tissues such as gums and allow for the gel to stay in place when positioned. As such, the gel can enhance the desired acoustic properties of the applied ultrasound devices and/or treatments. The ultrasound gel can have similar acoustic properties to the tissue it couples to, as ultrasound (sounds of a frequency higher than 20 kHz) propagates poorly through air.

In some embodiments, the gels can be tasteless (insipid) and do not stimulate salivary glands. The absence of taste in the mouth can reduce salivation which assists in reducing the amount of gel being washed by saliva and potentially ingested. Slight fragrance or flavors in the mouth can provide an increase in salivation which can be undesirable. In addition, the absence of taste can allow users to tolerate the gel in their mouths. In some embodiments, the gel can be mildly unpleasant in the mouth. As such, patients/users would be less likely to intentionally consume the gel.

In some embodiments, the gel manufacturing process can be done under vacuum to reduce/eliminate air trapped in the gel. The gel can be produced free of, or with a reduced amount of, air bubbles. In some embodiments, this characteristic can be achieved by vacuum mixing and manipulation during manufacturing.

Undissolved polymer or other insoluble particulate material can be avoided by thorough mixing, general adherence to GMP practices, and by using high grade compounds such as use of National Formulary (NF) standard compounds.

To achieve some or all of these properties, in some embodiments, the gel can comprise water, a neutralizer, a gelling/thickening agent, a preservative, a viscosity affecting agent, a radiation protective agent, a dental agent, and/or a colourant. In some embodiments, the colorant can be, for example, FD&C (Food, Drug, and Cosmetic) Green 3 colour powder, although any other safe coulorant known in the art could be used.

In some embodiments, the gel can be water-based, but not water soluble (hydrophobic) and therefore not readily dissolved by saliva. In addition, some embodiments of the gel do not dry out easily. In some embodiments, the water used in the gel can be demineralized, degassed, distilled and/or reverse osmosis. In addition, the water can be free of salts or alkali, as the presence of electrolyte can significantly reduce the viscosity of the gel. The water used in the gel can have low or acceptable levels of minerals, bacteria, etc. as would be known in the art.

In some embodiments, a neutralizer can be used to neutralize the pH of the gel to a biologically acceptable level. In some embodiments, a base can be used as a neutralizer, for instance potassium hydroxide (KOH), sodium hydroxide (NaOH), or triethanolamine. An appropriate amount of base can be used to obtain a final gel pH similar to saliva, in the range of 6.5+/−1, or in the range of 6+/−0.5. In some embodiments, KOH can be used (instead of NaOH) in order to minimize the viscosity loss/reduction due to the neutralizer, thereby maintaining high viscosity of the gel.

In some embodiments, the gel formulation can contain a gelling/thickening agent to increase the viscosity of the gel. In some embodiments, the gelling/thickening agent can be a carbomer. In some cases, the carbomer can be a Carbopol™. As known in the art, there are a variety of Carbopol™ polymer grades which differ in the performance characteristics (U.S. Pat. No. 4,002,221 by Buchalter, incorporated by reference herein in its entirety). In some cases, the Carbopol™ can be a highly cross-linked polymer such as a Carbopol™ 974P NF. Carbopol™ 974P NF can provide low irritancy and non-sensitizing properties. In addition, Carbopol™ 974P NF is generally not bio-absorbed or metabolized in the body due to the high molecular weight and can be cross-linked exhibiting high viscosities. Carbopol™ 974P NF concentrations of 0.1% to 5% by weight in the gel can be used in some embodiments to provide suitable viscosity for oral, or mucous membrane, use. As known in the art, these percentages can be measured as being relative to the weight of the water. That is, adding 1 gram of polymer to 100 grams of water would likely be known to those versed in the art as "1%". It can also be possible however, that one could have an alternate opinion, that a 1% solution is 1 gram dissolved in 99 grams of water, as this would have a total mass of 100 grams, giving what may be interpreted as a 1% solution. In this case, either interpretation can be allowed. In some embodiments, the Carbopol™ 974P NF concentration can be 1.3-1.8% by weight in the gel.

Carbopol 974P differs from other carbomers in the following ways:
a) Solvent used/safety: A significant area of difference among carbomers is the solvent system used to synthesize them.

"Traditional" polymers are synthesized in benzene (carcinogenic), such as 934 NF, 934P NF, 940 NF, 941 NF, 1342 NF. There are regulatory restrictions on the use of benzene in pharmaceutical formulations. In addition, according to Guidance for Industry Q3C guidelines, Benzene is grouped into Class 1 (Human Carcinogens).

"Toxicologically preferred" polymers are synthesized in either ethyl acetate or a cosolvent (ethyl acetate/cyclohexane mixture). As cyclohexane is classified as Class 2 solvents (non-genotoxic animal carcinogens or possible causative agents of irreversible toxicity, such as neurotoxicity or teratogenicity), Carbomers such as 980 NF, 981 NF, 5984 EP, ETD 2020 NF, Ultrez 10 NF were not desirable in the present gel applications.

Three carbomers (namely 71G NF, 971P NF, and 974P NF) use only Ethyl Acetate as a polymerization solvent.
  b) Viscosity: Among the three carbomers mentioned above (71G NF, 971P NF, and 974P NF), the viscosity of Carbopol 974P NF is 3-4 times higher than that of Carbopol 71G NF or 971P NF.
  c) Mucoadhesion: Carbopol 974P NF has the highest mucoahesive strength.

As such Carbopol™ 974P can be used in the present gels for the these reasons:
  1. It is safe for use in oral cavity or for intracavity ultrasound procedures, where the gel can be potentially ingested over a period of time (for oral use, a patient will continue ingesting this gel daily over many years).
  2. Among the carbomers that are safe for oral or intracavitary use, carbomer 974P has the highest viscosity for any given amount added to water. Further meaning that to achieve the same level of viscosity, the least amount of carbomer is used when using carbomer 974P, which further contributes to safety.
  3. Among the carbomers that are safe for oral or intracavitary use carbomer 974P has the highest mucoadhesive strength for any given amount added to water.

In addition, Glycerin can be used for increasing overall acoustic impedance of the gel, as well as to protect the gel from decreasing in viscosity after exposure to gamma irradiation.

In some embodiments, a preservative can also be added to the gel to preserve the gel and increase its safety for internal ultrasound applications. In some embodiments, the preservative can be a food grade preservative, for example, potassium sorbate, parabens, or monolaurin. Potassium sorbate can be used in the range of 0.01% to 1% of the gel to provide suitable preservation against common pathogens for a pH in the range of 3 to 6.5, or in the range of 6+/−0.5, which is also a common acidity range for saliva. In addition, other preservatives such as parabens can be used if a higher pH range is desired (for example, from pH 3 to 9). In some embodiments, the potassium sorbate concentration can be 0.1%. An acceptable daily ingestion intake of potassium sorbate can be 875 mg daily for an average adult of 70 kg. For some oral applications, only few grams of the gel can be used per day (for example, an estimated 3-5 grams per day). Assuming full ingestion and a potassium sorbate concentration of 0.1% of the gel, the daily dose would be on the order of few milligrams, which is well below the acceptable daily ingestion of 875 mg.

In some embodiments, a dental agent can be used in the gel to provide added dental benefits to a user/patient when the gel is used orally. In some embodiments, the dental agent can be a sugar alcohol. In some embodiments, the sugar alcohol can be xylitol. The dental agent can provide an additional treatment/therapeutic effect to a user/patient by preventing/reducing dental/oral bacteria and/or respiratory infections. For preventing dental decay, sugar alcohol, for instance xylitol in the range of 0.1% to 5% has been shown to reduce oral bacterial flora (for example *Streptococcus mutans*) and can lead to reduced risk of dental cavities and improved oral and dental health. A preferred concentration to reduce and prevent dental decay is 0.5% (this concentration was used in Kontiokari, T. et al. 1995. "Effect of Xylitol on Growth of Nasopharyngeal Bacteria In Vitro", Antimicrobial Agents and Chemotherapy. 39:1820, incorporated by reference herein in its entirety). Xylitol was also shown (same reference) to reduce bacteria in nasopharyngeal flora and reducing respiratory infections (for example inhibiting the growth of *Streptococcus pneumoniae*). In addition, xylitol is known to also have food preservation properties inhibiting the growth of microorganisms such as *Clostridium butyricum, Lactobacillus bulgaricus, Saccharomyces cerevisiae, Escherichia coli, Salmonella typhi* (Makinen, K. K. and Soderling, E. 1981. "Effect of Xylitol on Some Food-Spoilage Microorganisms", Journal of Food Science. 46:950, incorporated by reference herein in its entirety).

In some embodiments, a colorant (food, drug and/or cosmetic grade) could also be added to the gel if a colored gel is desired.

In some embodiments, CNC can be added to an "Adjusted Gel" formulation to increase overall viscosity of the gel, as well as to prevent breakdown of gel during irradiation, leading to a much lower decrease in overall viscosity post-irradiation. In some embodiments, both glycerin and CNC can be added together to an initial formulation for better protection from breakdown due to irradiation.

A CNC gel sample, as shown in Table 1 below, can be formulated by mixing Carbopol in water, allowing the mixture to stay overnight, then neutralizing with 18% KOH solution, followed by addition of CNC. Glycerin can also be added as a final additive. In CNC gels samples without Carbopol™, CNC can be simply mixed in water, followed by pH adjustment by adding a small amount of KOH solution. Glycerin can also be added as a final additive. The above gel samples can also have xylitol added as a dental agent, and potassium sorbate as a preservative.

An effect on post-radiation viscosity can also seen in a CNC hydrogel (i.e. no Carbopol in the formulation). CNC can accelerate the formation of hydrogels and can increase the effective crosslink density of hydrogels. CNC can be not only a reinforcing agent for hydrogel, but can also act as a multifunctional cross-linker for gelation.

Other concentrations of the gel components can also be used to obtain similar desired properties and results.

With regard to packaging and uses, the gels can be packed in sachet bags (for single or multiple uses), tubes (for single or multiple uses), or in bottles (squeeze bottles or bottle with pump), although any other appropriate packaging and/or dispensing means, as apparent to one skilled in the art, could be used. Prior art gel formulations, that risk spoilage and/or contamination with undesired microbes when the package is opened and exposed to air, are generally available in small, sterile pouches for single use. These are commonly used as lubricants or in situations where sterility is desired. As such, these prior art gel formulations are limited to single-use packaging. By contrast, some embodiments of the present gels do not have the same risk of spoilage, degradation, or contamination and can be packaged for multiple uses, adding increased convenience for the manufacturer and the user. In some embodiments, the intended uses of the presently disclosed gels do not necessarily require sterility.

In some embodiments, the gel can be used with ultrasound devices for ultrasound imaging and/or ultrasound treatment (therapy). Some examples of uses include methods of intraoral and dental ultrasound treatment (therapy in the oral cavity or the teeth/dental), methods of ultrasound imaging in the oral cavity (tongue, cheek, etc.) or dental ultrasound imaging, methods of internal imaging such as endorectal (transrectal) ultrasonography, transvaginal ultrasonography, or trans-esophageal echocardiography (ultrasound imaging of the heart through the food pipe). In addition, the gels can be used in general (non-ultrasound) dental applications, such as gels to improve denture comfort, to alleviate symptoms of dry mouth, and as a vehicle for chemical/pharmaceutical agents aimed at improving tooth and gum sensitivity or help the treatment of oral organs or food pipe organs where a gel is required. In some embodiments, imaging/therapy can be performed from outside of a mouth, where the imager/therapist adds gel (an external ultrasound gel as known in the art, or a gel as disclosed herein) in between the transducer and the cheek, and also an oral compatible gel (as disclosed herein) between the cheek and the dental organ for ultrasound coupling for imaging or therapy.

The specific properties of the gels provided herein can provide benefits in these types of applications. For example, the high viscosity of the gel can permit the gel to stay on an ultrasound transducer head and reach the target site, (particularly during intracavitary ultrasound procedures), whereas prior art gels are washed away or eroded by the body cavity prior to reaching the target site. The gels can be biocompatible with oral, food pipe, and vaginal and rectal mucous membrane tissue and fluids.

While the gels and uses thereof described herein are generally applicable to human imaging and therapy, the gels and uses thereof can also be applicable to veterinary ultrasound applications.

Without any limitation to the foregoing, the present gels and methods are further described by way of the following examples.

Example 1

Materials

Materials: Purified Water 1100 g, Carbopol 974P NF 13 g, Potassium Hydroxide 18 g, Club House™ green food colour 1 mL, Xylitol 5 g, Potassium sorbate 1 g, glycerine 50 g.

Equipment: Clock/Timer≥calibrated, Vacuum pump, 5/16" ID vacuum tubing, Vacuum chamber, Top-loading balance (0.1 g precision), Time-of-flight acoustic measurement system, pH meter+electrode, Brookfield™ viscometer.

General Supplies: Calculator, Spatula, Scoopula, Mixing vessel (eg. large jar or vat), Weighing paper, 50 mL plastic syringe—Luer-lock, Dropper bottle with dropper, Kim Wipes™, Paper towels, Label sheets, Pen, Felt marker, Anti-static brush, 50 mL beaker, Broad spatula.

Example 2

Production

Note that in some embodiments, mixing steps can be performed under vacuum so as to minimize gas/bubbles in the gel. If water or solutions are not previously degassed, the water or solution can be degassed prior to use so as to minimize gas/bubbles in the gel.

Prepare 18% KOH(aq) neutralizer: Weigh out 100 grams pure water into a small beaker. Weigh out 18 grams solid KOH into a beaker or onto a weighing paper. Slowly add solid KOH to water, allow to dissolve with occasional stirring (glass rod or plastic spatula). When fully dissolved, pour mixture into dropper bottle labelled as "18% KOH (aq)".

Prepare gel dispersion: Weigh out 900 grams water into mixing vessel (eg. 1000 mL beaker). Weigh out 5 grams xylitol. Dissolve xylitol in water with stirring. Weigh out 1 gram potassium sorbate. Dissolve potassium sorbate in xylitol solution above. Weigh out 13 grams Carbopol™ 974P NF. CAUTION: This material is a fluffy, lightweight powder. Ensure that any air currents are minimized and that all weighing surfaces are static free. Static can be minimized by light brushing of contacting surfaces with anti-static brush. Add Carbopol™ powder to potassium sorbate/xylitol solution above, with gentle manual mixing using a spatula. Allow the gel to hydrate, for example by allowing it to sit covered overnight in order to hydrate. *NOTE: the gel hydration can also be sped up by adding the Carbopol™ powder to a spinning volume of water, as with a magnetic stirrer.

Prepare gel: Add 42.9 grams of KOH solution above to a small beaker or other transfer vessel. The neutralizer solution should be added in a weight ratio of 3.3 grams neutralizer per gram of Carbopol™ powder. Add 42.9 grams KOH neutralizer solution to gel dispersion with manual stirring using broad spatula. Finally, add 50 g of glycerine to the gel dispersion. Mix until homogeneous gel is achieved. *NOTE: the gel will be highly viscous, making convection very difficult. Because of this, the mixing requires a lot of physical mixing. Unless the entire volume of the gel is thoroughly mixed, there will be regions of differing pH. Confirm pH is approximately 6.0 using a standard pH meter. With a pH meter, after calibrating the meter, dip the electrode into the gel and stir it around briefly to coat the electrode in gel, then take a reading. Take a few readings, mixing in between. If the readings are inconsistent, mix the gel thoroughly and check again. If the readings were inconsistent on a sample volume, then it is likely that the entire batch is not properly mixed. Target pH=6.0±0.2. If the pH is low, add neutralizer in appropriate increments until pH is in correct range. Note that the readings will not be consistent without extremely thorough mixing. If desired, add an acceptable colourant to the gel, for example add FD&C (Food, Drug, and Cosmetic) Green 3 colour powder to gel. Mix until colour is evenly dispersed. This will take thorough mixing with a broad spatula, or mixing by pallets in an industrial mixing chamber, under a vacuum.

Degas gel: The degassing step is intended to remove bubbles introduced in the formulation process. Place the gel in an open container. Place this container into the vacuum chamber, seal the chamber, and pump down to 600 mm Hg for 10 minutes (stopwatch). Allow the gel to warm up to room temperature before making any further measurements.

A CNC gel sample, as shown in Table 1 below, can be formulated by mixing Carbopol in water, allowing the mixture to stay overnight, then neutralizing with 18% KOH solution, followed by addition of CNC. Glycerin can also be added as a final additive. In CNC gels samples without Carbopol™, CNC can be simply mixed in water, followed by pH adjustment by adding a small amount of KOH solution. Glycerin can also be added as a final additive. The above gel samples can also have xylitol added as a dental agent, and potassium sorbate as a preservative.

Characterize gel density: Multiple methods to characterize gel density are known in the art and can be used. In one example, draw some degassed gel into a 50 mL syringe, avoiding drawing in air bubbles as much as possible. Use some easily readable part of the piston to make an initial reading of volume. *Note that the total volume is not important, only the difference between the initial and final volume readings. Wipe all excess gel from the outside of the syringe using a paper towel or KimWipe™, then weigh the syringe. Draw some more degassed gel into the syringe, studiously avoiding drawing in air bubbles. The more gel used here, the lower the relative error, so get at least 10 mL of gel on top of the initial amount. Record the final volume measurement using the same part of the piston as was used for the initial measurement. Wipe all excess gel from the outside of the syringe using a paper towel or Kim Wipe™, and then weigh the syringe. Typical values are in the range 1.0-1.1 g/mL, with most readings around 1.045 g/ml.

Characterize gel acoustic velocity: Multiple methods to characterize gel acoustic velocity are known in the art and can be used. In one example, using a spatula or something similar, fill the time-of-flight device with gel. One example of an in-house time-of-flight device can be a plastic cylinder with a length of approximately 100 mm, with an ultrasound transducer attached to one end, and a thin sheet of metal attached at the other end. The tube can be filled with gel, the transducer can generate short ultrasound pulses when driven by a function generator, the transducer can sense a returning ultrasound pulse when connected to an oscilloscope, and the thin metal sheet can work as an ultrasound reflector. Place the device in the vacuum chamber and degas as before. There should be no bubbles or air gaps in the gel during the measurement. Use the function generator and digital oscilloscope to record the time of flight. Using the in-house apparatus, typical values for the acoustic velocity can be in the range of 1450-1550 m/s.

Calculate acoustic impedance: Calculations were done based on in-house device although multiple methods to calculate acoustic impedance are known in the art and can be used. In one example, Impedance=(density)(acoustic velocity). Typical values calculated in-house have ranged from 1.45-1.60 MRayls, although other values are possible.

Packaging and Quality Control: Dispense gel into final packaging, which can be a multiple use packaging like bottles, jars, etc, or single use sterile or non-sterile pouches. Viscosity testing: The viscosity determined for the gel at pH 6 was 50,000 to 100,000+ mPa·s (or cPs), and 85,000 mPa·s (or cP) in one sample [at 37° C. using Brookfield™ Viscometer LVF, S/N: C3390 spindle #4, 6 rpm]. This can be a target spec, although deviations may occur in different circumstances and when scaling up production. Viscosity can be difficult to quantify and measure and the measurement can be dependent on the measuring apparatus used and the conditions under what the viscosity is measured. Having said that, one skilled in the art would have a working knowledge of the relative viscosity of a gel with high viscosity.

Example 3

Results: Viscosity Testing and Stability

TABLE 1

Effects of Radiation on Viscosity

| Sample* | Gamma radiation dose (kGy) | Acoustic Impedance post radiation (MRayl) | Pre-radiation viscosity (cPs) | Post-radiation viscosity (cPs) | Formulation used |
|---|---|---|---|---|---|
| Initial gel | 40-48 KGy (Maximum Gamma Radiation Level test) | ~1.5 | >100.000 | fluid <10,000 | 1.3 g Carbopol, NO glycerine, NO CNC |
| Adjusted Gel | 36.6-41.7 KGy | 1.49 | 94500 | 57,750 | 1.3 g Carbopol, 5 g glycerine, NO CNC |
| Adjusted gel | 27.6-32.8 KGy | 1.590 | 94500 | 85.000 65.000 (after 11 months aging) | 1.8 g Carbopol, 9.5 g glycerine, NO CNC |
| CNC gel 6 | 40-49.5 | 1.540 | >100,000 | 41,000 | 1.3 g Carbopol, 5 g glycerine, NO CNC |
| CNC gel 1 | 40-49.5 | 1.517 | >100,000 | 86,000 | 1.3 g Carbopol, 5 g glycerine, 2 g CNC |
| CNC gel 8 | 40-49.5 | 1.519 | >100,000 | 8000 | 1.3 g Carbopol, NO glycerine, 2 g CNC |
| CNC gel 2 | 40-49.5 | 1.498 | >100,000 | >100,000 | 1.3 g Carbopol, 5 g glycerine, 4 g CNC |
| CNC gel 9 | 40-49.5 | 1.539 | >100,000 | 52,000 | 1.3 g Carbopol, NO glycerine, 4 g CNC |
| CNC gel 3 | 40-49.5 | 1.587 | >100,000 | >100,000 | 1.3 g Carbopol, 5 g glycerine, 6 g CNC |
| CNC gel 10 | 40-49.5 | 1.521 | >100,000 | 91,000 | 1.3 g Carbopol, NO glycerine, 6 g CNC |
| CNC gel 7 | 40-49.5 | 1.616 | appears similar but lower than CNC gel11 | 73,000 | NO Carbopol, 5 g glycerin, 15 g CNC |
| CNC gel 11 | 40-49.5 | 1.575 | 39,000 | >100,000 | NO Carbopol, NO glycerine, 15 g CNC |

*All gel samples from Table 1 were adjusted to have a pH of 6 using 18% Potassium Hydroxide solution. The above samples are water-based, and also contain 0.5% xylitol as a dental agent, and 0.1% potassium sorbate as a preservative.

Example 4

Observations: CNC and Gel Viscosity

Certain observations were made regarding the creation, irradiation, and viscosity testing of the gel samples, as outlined in Table 1.
1) Glycerin can help maintain crosslinking of Carbopol™ gels, but not of pure CNC gels during gamma radiation;
2) CNC can provide crosslinking protection against breakdown due to gamma radiation in the case of Carbopol™ gels with or without glycerin;
3) CNC and glycerin both added to the "Adjusted Gel" formulation can result in gels with the least drop in viscosity after irradiation;
4) Glycerin can increase the acoustic impedance of a gel, but adding glycerin is often needed to maintain gel viscosity after radiation. However, adding CNC does not appear to change the acoustic impedance, and only protects the gel viscosity;
5) Pure CNC gels can present an acoustic impedance too high for coupling to soft tissue, but adding less than 15% CNC can result in both a viscous gel and desired acoustic impedance;
6) Certain concentrations of CNC gels can show an increase in viscosity after irradiation (for example, see results of CNC Sample 11 in Table 1); and
7) Adding glycerin adds a sweet taste to the gel, while adding CNC adds no taste.

Example 5

Conclusions: Crystalline Nanocellulose (CNC) and Gel Viscosity

In some embodiments, CNC can be added to an "Adjusted Gel" formulation to increase overall viscosity of the gel, as well as to prevent breakdown of gel during irradiation, leading to a much lower decrease in overall viscosity post-irradiation. In some embodiments, both glycerin and CNC can be added together to an initial formulation for better protection from breakdown due to irradiation.

An effect on post-radiation viscosity can also seen in a CNC hydrogel (i.e. no Carbopol in the formulation). CNC can accelerate the formation of hydrogels and can increase the effective crosslink density of hydrogels. CNC can be not only a reinforcing agent for hydrogel, but can also act as a multifunctional cross-linker for gelation.

The scope of the claims should not be limited by the embodiments as set forth in the examples herein, but should be given the broadest interpretation consistent with the description as a whole.

Although a few embodiments have been shown and described, it will be appreciated by those skilled in the art that various changes and modifications can be made to the embodiments described herein. The terms and expressions used in the above description have been used herein as terms of description and not of limitation, and there is no intention in the use of such terms and expressions of excluding equivalents of the features shown and described or portions thereof, it being recognized that the invention is defined and limited only by the claims that follow.

The teachings provided herein can be applied to other methods, not necessarily the method described herein. The elements and acts of the various embodiments described above can be combined to provide further embodiments.

These and other changes can be made to the invention in light of the above description. While the above description details certain embodiments of the invention and describes certain embodiments, no matter how detailed the above appears in text, the invention can be practiced in many ways. Details of the method may vary considerably in their implementation details, while still being encompassed by the invention disclosed herein.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification. Accordingly, the actual scope of the invention encompasses not only the disclosed embodiments, but also all equivalent ways of practicing or implementing the invention.

The above description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. The elements and acts of the various embodiments described above can be combined to provide further embodiments.

While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

REFERENCES

The following references are hereby incorporated by reference into this application in their entirety.
1. U.S. Provisional Application No. 61/740,408, entitled "Internal Ultrasound Gel", filed on Dec. 20, 2012.
2. PCT International Application No.: PCT/CA2013/001058, Pub. No.: WO/2014/094127, entitled "Internal Ultrasound Gel", filed on Dec. 18, 2013.
3. Modification and Characterization of Biodegradable Methylcellulose Films with TrimethylolpropaneTrimethacrylate (TMPTMA) by γ Radiation: Effect of Nanocrystalline Cellulose. J. Agric. Food Chem., 60(2012): 623-629;
4. Mechanical and Barrier Properties of Nanocrystalline Cellulose Reinforced Poly(caprolactone) Composites: Effect of Gamma Radiation. J. Applied Polym. Sci., 129(2013): 3038-2046;
5. Radiation grafting on natural films. Rad Phys. And Chem., 94(2014): 88-92.
6. U.S. Pat. No. 8,618,1752, Ultrasound medical gel composition etherified hydroxyethylcellulose;
7. U.S. Pat. No. 3,108,890, Aqueous Cellulosic Compositions and Methods of Making Same;
8. Comparison of Gamma Radiation Crosslinking and Chemical Crosslinking on Properties of Methylcellulose Hydrogel. Engineering Journal, Col 16(4): pp. 15-28 ("Rimdusit et al.).
9. Sultana, Islam, Dafader and Haque. Preparation of carboxymethyl cellulose/acrylamide Copolymer hydrogel using gamma radiation and Investigation of its swelling behavior. Journal of Bangladesh Chemical Society, Vol. 25(2), 132-138, 2012.

10. Xiaoyun Qiu and Shuwen Hu. "Smart" Materials Based on Cellulose: A Review of the
11. Preparations, Properties, and Applications. Materials 2013, 6, 738-781; doi:10.3390/ma6030738
12. Chengjun Zhou, Qinglin Wua, Yiying Yue, Quanguo Zhang. Application of rod-shaped cellulose nanocrystals in polyacrylamide hydrogels. Journal of Colloid and Interface Science 353 (2011) 116-123
13. B. L. Peng, N. Dhar, H. L. Liu, and K. C. Tam. Chemistry and Applications of Nanocrystalline Cellulose and its Derivatives: a Nanotechnology Perspective. The Canadian Journal of Chemical Engineering Volume 9999, 2011.
14. Chengjun Zhou and Qinglin Wu. Recent Development in Applications of Cellulose Nanocrystals for Advanced Polymer-Based Nanocomposites by Novel Fabrication Strategies.
15. Alessandro Sannino, Christian Demitri and Marta Madaghiele. Biodegradable Cellulose-based Hydrogels: Design and Applications. Materials 2009, 2, 353-373; doi:10.3390/ma2020353
16. Canadian Patent Application Number 2,770,837
17. Canadian Patent Number 2,312,614
18. US Patent Application Number 2006/0281045
19. US Patent Application Number 2008/0311545
20. US Patent Application Number 2010/0124732
21. US Patent Application Number 2012/0040312
22. U.S. Pat. No. 4,002,221
23. U.S. Pat. No. 7,004,933
24. U.S. Pat. No. 7,070,565
25. U.S. Pat. No. 7,078,015
26. U.S. Pat. No. 7,269,873
27. U.S. Pat. No. 7,285,093
28. U.S. Pat. No. 8,273,024
29. Makinen, K. K. and Soderling, E. 1981. "Effect of Xylitol on Some Food-Spoilage Microorganisms", Journal of Food Science. 46:950.
30. Kontiokari, T. et al. 1995. "Effect of Xylitol on Growth of Nasopharyngeal Bacteria In Vitro", Antimicrobial Agents and Chemotherapy. 39:1820.

We claim:

1. A food grade intra-oral ultrasound coupling gel comprising:
   water;
   a thickening agent for thickening the water into a gel, the thickening agent comprising a carbomer, wherein the carbomer is at a concentration of between 0.1% and 5% of the gel by weight;
   a neutralizer for adjusting a pH level of the gel;
   a viscosity agent for reducing changes of gel viscosity due to gamma radiation exposure, the viscosity agent comprising cellulose nanocrystals (CNC) and glycerin, wherein the CNC is at a concentration of between 2% and 15% of the gel by weight and wherein the glycerin is at a concentration of between 5% and 10% of the gel by weight;
   wherein the gel has been exposed to gamma radiation;
   wherein the gel has a post-radiation viscosity between 50,000 and 100,000 cPs when measured using a viscometer at 37° C.; and
   wherein the gel has an acoustic impedance similar to soft tissue and is safe for ingestion.

2. The gel of claim 1 wherein the carbomer comprises carbomer homopolymer Type B.

3. The gel of claim 1 wherein the neutralizer comprises a base selected from the group consisting of potassium hydroxide, sodium hydroxide, and triethanolamine.

4. The gel of claim 1 wherein the pH level of the gel is between 5.8 and 6.4.

5. The gel of claim 1 further comprising a dental agent for inhibiting growth of dental microorganisms.

6. The gel of claim 5 wherein the dental agent is a sugar alcohol.

7. The gel of claim 6 wherein the sugar alcohol is xylitol.

8. The gel of claim 1 further comprising a colourant for colouring the gel.

9. The gel of claim 1, further comprising a preservative.

10. The gel of claim 9, wherein the preservative comprises a food grade preservative.

11. The gel of claim 9, wherein the preservative comprises potassium sorbate.

* * * * *